US008669235B2

(12) United States Patent (10) Patent No.: US 8,669,235 B2
Baltimore et al. (45) Date of Patent: Mar. 11, 2014

(54) MODULATION OF INNATE IMMUNITY RECEPTORS' SIGNALING BY MICRORNAS MIR-146A AND MIR-146B

(75) Inventors: David Baltimore, Pasadena, CA (US); Mark Boldin, Pasadena, CA (US); Konstantin Taganov, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 629 days.

(21) Appl. No.: 11/690,105

(22) Filed: Mar. 22, 2007

(65) Prior Publication Data

US 2007/0232553 A1 Oct. 4, 2007

Related U.S. Application Data

(60) Provisional application No. 60/785,394, filed on Mar. 23, 2006.

(51) Int. Cl.
*A61K 48/00* (2006.01)
*C12N 15/00* (2006.01)
*C07H 21/04* (2006.01)
*C12N 5/00* (2006.01)

(52) U.S. Cl.
USPC ....... 514/44 R; 536/23.1; 536/24.5; 435/375; 435/440

(58) Field of Classification Search
USPC ............. 435/4, 6, 375; 536/23.1, 24.5, 25.33; 800/14
See application file for complete search history.

(56) References Cited

U.S. PATENT DOCUMENTS

| 7,670,840 B2 * | 3/2010 | Croce et al. ................. 436/6 |
|---|---|---|
| 2005/0261218 A1 | 11/2005 | Esau et al. |
| 2005/0267300 A1 * | 12/2005 | Manoharan et al. ........ 536/25.33 |
| 2006/0058266 A1 * | 3/2006 | Manoharan et al. ............ 514/81 |
| 2006/0185027 A1 * | 8/2006 | Bartel et al. ..................... 800/14 |
| 2007/0092882 A1 * | 4/2007 | Wang et al. ........................ 435/6 |
| 2009/0124566 A1 * | 5/2009 | Chi et al. ........................ 514/44 |

OTHER PUBLICATIONS

O'Neill et al., Signal transduction pathways activated by the IL-1 receptor family: ancient signaling machinery in mammals, insects, and plants, Jun. 1998, Journal of Leukocyte Biology, vol. 63, pp. 650-657.*
Andreakos et al., Is targeting Toll-like receptors and their signaling pathway a useful therapeutic approach to modulating cytokine-driven inflammation? 2004, Immunological Reviews, vol. 202, pp. 250-265.*
Gogolak et al., Targeting dendritic cells for priming cellular immune responses, 2003, Journal of Molecular Recognition, vol. 16, pp. 299-317.*

Wang et al., Progress in the delivery of therapeutic oligonucleotides: Organ/Cellular distribution and targeted delivery of oligonucleotides in vivo, 2003, Antisense and Nucleic Acid Drug Development, vol. 13, pp. 169-189.*
Patil et al., DNA-based therapeutics and DNA delivery systems: A comprehensive review, 2005, The AAPS Journal, vol. 7, pp. E61-E77.*
TargetScan output for "miR-146" using "TargetScan: Prediction of microRNA targets", Copyright © 2003, last modified, Thursday, Jun. 30, 2005. Accessed http://genes.mit.edu/tscan/targetsancS.html on Jan. 25, 2010. nine printed pages are enclosed.*
Human miRNA targets, miRanda webserver, microrna.org, Apr. 2005 version, last updated on Jun. 5, 2005. Accessed http://cbio.mskcc.org/cgi-bin/mirnavierwer/ on Jan. 25, 2010. one printed page is enclosed.*
Esau et al., "miR-122 regulation of lipid metabolism revealed by in vivo antisense targeting", 2006, Cell Metabolism, vol. 3, pp. 87-98.*
"TargetScan output" for miR-122, "TargetScan" version 2.1,last modified on Jun. 30, 2005, accessed http://genes.mit.edu/tscan/targetscanS.html on Oct. 24, 2010. A total of 28 print-out pages are enclosed.*
Krichevsky et al., Specific microRNAs modulate embryonic stem cell-derived neurogenesis, 2006, Stem Cells, vol. 24, pp. 857-864.*
Akira et al., "A nuclear factor for Israel-6 expression (NF-IL6) is a member of a C/EBP family," *Embo J* 9: 1897-906 (1990).
Ambion ® "Functional Analysis/Anti-miR™ miRNA Inhibitors" Ambion ® miRNA Research Guide, p. 12.
Ambros "The Functions of Animal MicroRNAs," *Nature* 431: 350-355 (2004).
Bartel "MicroRNAs: Genomics, Biogenesis, Mechanism, and Function," *Cell* 116: 281-297 (2004).
Bentwich et al., "Identification of hundreds of conserved and nonconserved human microRNAs," *Nat. Genet* 37, 766-70 (2005).
Cai et al., "Kaposi's sarcoma-associated herpesvirus expresses an array of viral microRNAs in latently infected cells," *Proc Natl Acad Sci USA* 102: 5570-5 (2005).
Calin et al., "Human microRNA genes are frequently located at fragile sites and genomic regions involved in cancers," *Proc Natl Acad Sci USA* 101, 2999-3004 (2004).
Chen et al., "MicroRNAs Modulate Hematopoietic Lineage Differentiation," *Science* 303, 83-6 (2004).
Chendrimada et al., "TRBP Recruits the Dicer Complex to Ago2 for MicroRNA Processing and Gene Silencing," *Nature* 436: 740-744 (2005).
Couzin, "Small RNAs Make Big Splash," *Science* 298(5602): 2296-7 (2002).

(Continued)

*Primary Examiner* — Dana Shin
(74) *Attorney, Agent, or Firm* — Knobbe, Martens, Olson & Bear, LLP

(57) ABSTRACT

The present disclosure relates to the finding that microRNA-146 plays a role modulating the innate immune response. Innate immunity receptor signaling can be modulated by delivery of microRNA-146 (miR-146) or antisense miR-146 to target immune cells. In some embodiments, IL-1 receptor associated kinase 1 (IRAK1) and TNF receptor associated factor 6 (TRAF6) expression levels are downregulated in a target cell by administering a miR-146 oligonucleotide. Modulation of the innate immune system through miR-146 can be used to treat a variety of diseases and disorders associated with activation of the innate immune system, such as sepsis and Crohn's disease.

11 Claims, 4 Drawing Sheets

(56) References Cited

OTHER PUBLICATIONS

Dennis, "Small RNAs—The genome's guiding hand?," *Nature* 420(6917): 732 (2002).
Dumitru et al., "TNF—a Induction by LPS Is Regulated Post-transcriptionally via a Tpl2/ERK-Dependent Pathway," *Cell* 103, 1071-83 (2000).
Esau et al., ",", *J Biol Chem* 279, 52361-5 (2004).
Farh et al., "The Widespread Impact of Mammalian MicroRNAs on mRNA Repression and Evolution," *Science* 310: 1817-1821 (2005).
Fazi et al., "A Minicircuitry Comprised of MicroRNA-223 and Transcription Factors NFI-A and C/EBPaRegulatesHumanGranulopoiesis," *Cell* 819-831 (2005).
Ghosh et al., "NF-Kappa B and Rel Proteins: evolutionary conserved mediators of immune responses," *Annu Rev Immunol* 16: 225-60 (1998).
Gregory et al., "The Microprocessor Complex Mediates the Genesis of MicroRNAs," *Nature* 432: 235-240 (2004).
Griffiths-Jones et al., "miRBase: microRNA sequences, targets and gene nomenclature,"*Acids Res* 34, D140-4 (2006).
He et al., "A microRNA polycistron as a potential human oncogene," *Nature* 435, 828-33 (2005).
John et al., "Human MicroRNA Targets," *PLOS Biol* 2, e363 (2004).
Kinger and Martiennsen, "Macro effects of microRNAs in plants," *Trends in Genetics* 19(1): 13-6 (2003).
Krek et al., "Combinatorial microRNA target predictions," *Nat Genet* 37, 495-500 (2005).
Krutzfeldt et al., "Silencing of microRNAs in vivo with 'antagomirs'," *Nature* 438, 685-9 (2005).
Lecellier et al., "A Cellular MicroRNA Mediates Antiviral Defense in Human Cells," *Science* 308, 557-60 (2005).
Lee et al., "MicroRNA Genes are Transcribed by RNA Polymerase II," *EMBO J* 23: 4051-4060 (2004).
Lewis et al., "Prediction of Mammalian MicroRNA Targets," *Cell* 115, 787-98 (2003).
Lin et al., "Selective DNA binding and association with the CREB binding protein coactivator contribute to differential activation of alpha/beta interferon genes by interferon regulatory factors 3 and 7," *Mol cell Biol* 20: 6342-53 (2000).
Lu et al., "MicroRNA expression profiles classify human cancers," *Nature* 435, 834-8 (2005).
Mateucci, et al., "Synthesis of Deoxyoligonucleotides on a Polymer Support," *J. Am. Chem. Soc.* 103:3185-3191 (1981).
Monticelli et al., "MicroRNA profiling of the murine hematopoietic system," *Genome Biol* 6, R71 (2005).
O'Connel et al., "MicroRNA-155 is Induced During the Macrophage Inflammatory Response," Proceedings of the National Academy of Sciences of the United States of America 104(5): 1604-1609 (2007).
O'Donnel et al., "c-Myc-regulated microRNAs modulate E2F1 expression," *Nature* 435: 839-843 (2005).
Pasquinelli et al., "MicroRNAs: a developing story," *Curr Opin Genet Dev* 15: 200-205 (2005).
Poltarok et al., "Defective LPS Signaling in C3H/HeJ and C57BL/10ScCr Mice: Mutations in TIr4 Gene," *Science* 282: 2085-8 (1998).
Poy et al., "A pancreatic islet-specific microRNA regulates insulin secretion," *Nature* 432, 226-30 (2004).
Qin "SIGIRR inhibits interleukin-1 receptor- and toll-like receptor 4-medicated signaling through different mechamisms." *J Biol Chem* 280: 25233-41 (2005).
Sullivan and Ganem "MicroRNAs and Viral Infection," *Mol Cell* 20, 3-7 (2005).
Taganov et al., "NF-kB-dependent Induction of MicroRNA miR-146, an Inhibitor Targeted to Signaling Proteins of Innate Immune Responses," Proceedings of the National Academy of Sciences of the United States of America 103(33): 12481-12486 (2006).
Takeda et al., "Toll-Like Receptors," *Annu Rev Immunol* 21, 335-76 (2003).
Zeng & Cullen, "Sequence requirements for micro RNA processing and function in human cells," *RNA*, 9(1): 112-123 (2003).
Akira et al., "Toll-like receptor signaling," *Nature Reviews Immunology*, Jul. 2004, 4(7):499-511.
Bentwich et al., "Identification of hundreds of conserved and nonconserved human microRNAs," *Nature Genetics* Jul. 2005, 37:766-770.
He et al., "The role of microRNA genes in papillary thyroid carcinoma," *PNAS* Dec. 2005, 102(52):19075-19080.
Bentwich, Isaac. Prediction and validation of microRNAs and their targets. FEBS Letters. 579:5904-5910 (2005).
Desmet et al. "Selective Blockade of NF-kB Activity in airway Immune Cells Inhibits the Effector Phase of Experimental Asthma." Journal of Immunology. 5766-5775 (2004).
Finotto et al. "Treatment of Allergic Airway Inflammation and Hyperresponsiveness by Antisense-induced Local Blockade of GATA-3 Expression." J. Exp. Med. 193(11): 1247-1260 (2001).
Immunology. W.H. Freeman & Co. NY. Kuby ed. "Cells and Organs of the Immune System." Chp. 3. 39-59 (1992).
Myers et al. "Antisense oligonucleotide blockade of alpha 4 integrin prevents and reverses clinical symptoms in murine experimental autoimmune encephalomyelitis." Journal of Neuroimmunology 160:12-24 (2005).
Myers et al. "Antisense Oligonucleotide Blockade of Tumor Necrosis Factor-α in Two Murine Models of Colitis." Journal of Pharmacology and Experimental Therapeutics. 304(1):411-424 (2003).
Schlaak et al. "Antisense Phosphorothioate Oligonucleotides to the p65 Subunit of NF-kB Abrogate Fulminant Septic Shock Induced by *S. typhimurium* in Mice." Scand. J. Immunol. 54:396-403 (2001).
Sethupathy et al. "A guide through present computational approaches for the identification of mammalian microRNA targets." Nature Methods. 3(11):881-886 (2006).
Xu Xiegun. "Same computational analysis, different miRNA target predictions." Nature Methods. 4(3):191 (2007).
Zhang et al. "Computational identification of microRNAs and their targets." Computational Biology and Chemistry. 30:395-407 (2006).
Calin et al. "A MicroRNA Signature Associated with Prognosis and Progression in Chronic Lymphocytic Leukemia." New England Journal of Medicine. 353(17):1793-1801 (2005).
Hirata et al. "MyD88 and TNF receptor-associated factor 6 are critical signal transducers in Helicobacter pylori-Infected Human Epithelial Cells." Journal of Immunology. 176(6):3796-3803 (2006).
Opitz et al. "Nucleotide-binding oligomerization domain proteins are innate immune receptors for internalized *Streptococcus pneumoniae*." Journal of Biological Chemistry. 279(35):36426-36432 (2004).
Sun et al. "The TRAF6 ubiquitin ligase and TAK1 Kinase Mediate IKK Activation by BCL10 and MALT1 in T Lymphocytes." Molecular Cell. 14:289-301 (2004).
European Search Report for European Application No. 07773467.1 dated Nov. 25, 2010.

\* cited by examiner

Figure 3 a

```
5' - UGCUCUAGAAAGUUGAGUUCUCA    TRAF6-wt        (SEQ ID NO: 40)
         | | |   | | |  | |  | | | | | | | |
3' - UUGGGUACCUU-AAGUCAAGAGU    mir-146a        (SEQ ID NO: 41)
         | | | |   | | |  | | |       | |
5' - UGCUCUAGAAAGUUGAGaagaCA    TRAF6-mut       (SEQ ID NO: 42)
```

```
5' - CCCCCAA^AUCC GGAAGUC^AA AGUUCUCA    IRAK1_site#1-wt    (SEQ ID NO: 43)
       | | | |         | | | |  | |     | | | | | | | |
3' - UUGGGUA----CCUUAAG--UCAAGAGU        mir-146a           (SEQ ID NO: 41)
       | | | |         | | | |  | |         | |
5' - CCCCCAA_AUCC GGAAGUC_AA AGaagaCA    IRAK1_site#1-mut   (SEQ ID NO: 44)
```

```
5' - UUCUCAUGGUCAGAAGUUCUCA    IRAK1_site#2-wt   (SEQ ID NO: 45)
       | | | | | | | |    | | | | | | | |
3' - UUGGGUACCUUAAGUCAAGAGU    mir-146a          (SEQ ID NO: 41)
       | | | | | | | |    | |     | |
5' - UUCUCAUGGUCAGAAGaagaCA    IRAK1_site#2-mut  (SEQ ID NO: 46)
``` b

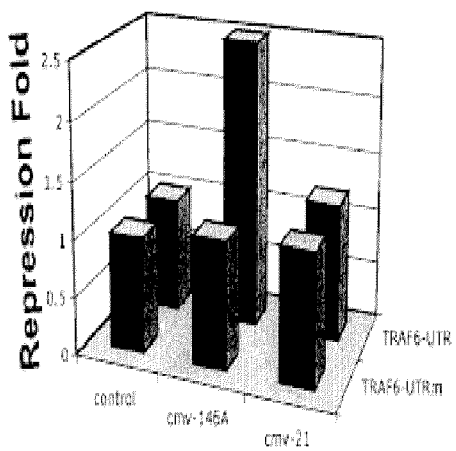

c

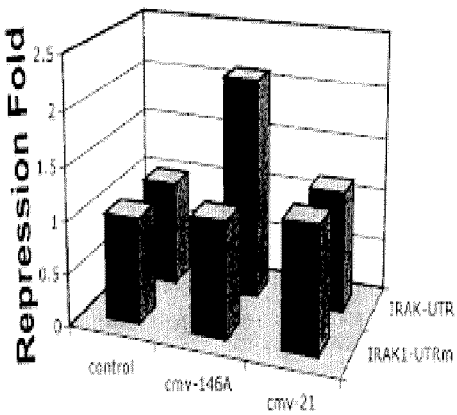

SEQUENCE LISTING

<160> NUMBER OF SEQ ID NOS: 46

<210> SEQ ID NO 1
<211> LENGTH: 22
<212> TYPE: RNA
<213> ORGANISM: Homo sapien

<400> SEQUENCE: 1
ugagaacuga auuccaugggg uu                                              22

<210> SEQ ID NO 2
<211> LENGTH: 99
<212> TYPE: RNA
<213> ORGANISM: Homo sapien

<400> SEQUENCE: 2
ccgaugugua uccucagcuu ugagaacuga auuccauggg uugugucagu gucagaccuc      60
ugaaauucag uucuucagcu gggauaucuc ugucaucgu                             99

<210> SEQ ID NO 3
<211> LENGTH: 22
<212> TYPE: RNA
<213> ORGANISM: Homo sapien

<400> SEQUENCE: 3
ugagaacuga auuccauagg cu                                               22

<210> SEQ ID NO 4
<211> LENGTH: 73
<212> TYPE: RNA
<213> ORGANISM: Homo sapien

<400> SEQUENCE: 4
ccuggcacug agaacugaau uccauaggcu gugagcucua gcaaugcccu guggacucag      60
uucuggugcc cgg                                                         73

<210> SEQ ID NO 5
<211> LENGTH: 22
<212> TYPE: DNA
<213> ORGANISM: Homo sapien

<400> SEQUENCE: 5
tgagaactga attccatggg tt                                               22

<210> SEQ ID NO 6
<211> LENGTH: 99
<212> TYPE: DNA
<213> ORGANISM: Homo sapien

<400> SEQUENCE: 6
ccgatgtgta tcctcagctt tgagaactga attccatggg ttgtgtcagt gtcagacctc      60
tgaaattcag ttcttcagct gggatatctc tgtcatcgt                             99

<210> SEQ ID NO 7
<211> LENGTH: 22

```
<212> TYPE: DNA
<213> ORGANISM: Homo sapien

<400> SEQUENCE: 7
tgagaactga attccatagg ct                                              22

<210> SEQ ID NO 8
<211> LENGTH: 73
<212> TYPE: DNA
<213> ORGANISM: Homo sapien

<400> SEQUENCE: 8
cctggcactg agaactgaat tccataggct gtgagctcta gcaatgccct gtggactcag     60
ttctggtgcc cgg                                                        73

<210> SEQ ID NO 9
<211> LENGTH: 22
<212> TYPE: RNA
<213> ORGANISM: Artificial Sequence
<220> FEATURE:
<223> OTHER INFORMATION: Anti-sense miR-146a

<400> SEQUENCE: 9
aacccaugga auucaguucu ca                                              22

<210> SEQ ID NO 10
<211> LENGTH: 22
<212> TYPE: RNA
<213> ORGANISM: Artificial Sequence
<220> FEATURE:
<223> OTHER INFORMATION: Anti-sense miR-146b

<400> SEQUENCE: 10
agccuaugga auucaguucu ca                                              22

<210> SEQ ID NO 11
<211> LENGTH: 22
<212> TYPE: DNA
<213> ORGANISM: Artificial Sequence
<220> FEATURE:
<223> OTHER INFORMATION: Anti-sense miR-146a

<400> SEQUENCE: 11
aacccatgga attcagttct ca                                              22

<210> SEQ ID NO 12
<211> LENGTH: 22
<212> TYPE: DNA
<213> ORGANISM: Artificial Sequence
<220> FEATURE:
<223> OTHER INFORMATION: Anti-sense miR-146b

<400> SEQUENCE: 12
agcctatgga attcagttct ca                                              22

<210> SEQ ID NO 13
<211> LENGTH: 2337
<212> TYPE: DNA
<213> ORGANISM: Homo sapien

<400> SEQUENCE: 13
tctccaagac gcttgaccgc tcttcctttc ctggatggca ccagcagggc cgattggagt     60
ggtaaaccct gggccggaag gcatgccaaa gggtggacag gatggacagg agacagtagc    120
acaacgagga gggggagaac agtggctgaa ttggaaatga taaataaaa tgaaatttta    180
```

```
ggagctcgct ggctgggaca ggcctggact gcaaggaggg gtctttgcac catctctgaa    240
aagccgatgt gtatcctcag cttttgagaac tgaattccat gggttgtgtc agtgtcagac    300
ctgtgaaatt cagttcttca gctgggatat ctctgtcatc gtgggcttga ggacctggag    360
agagtagatc ctgaagaact ttttcagtct gctgaagagc ttggaagact ggagacagaa    420
ggcagagtct caggctctga aggtataagg agtgtgagtt cctgtgagaa acactcattt    480
gattgtgaaa agacttgaat tctatgctaa gcagggttcc aagtagctaa atgaatgatc    540
tcagcaagtc tctcttgctg ctgctgctac tcgtttacat ttattgatta cttacgatga    600
ttcaggtact gttgtaagtg ctttacatgc tgttatacga gactcttggg agaaatcact    660
ttaatgaagc ttgagacaca tggcattgcc atgcaatgat ttttccccccc tcttcacggg    720 atcagaggga actaatagaa tgtgacaatg attctttagc agggactgct gaggcttctg    780 gttcctttt aagatctgca gtgaaagaag atgagaaaca tggatatgcc cttcttttgg    840
tccccctctt cctttatttg atctctactt ccttctataa atatattagg gctacattgt    900 cccttgtat ttcaaacaag gcaaaaagag gttgtaatta cactttactg caatcctcag    960
tttctccagg gaacaggaat gcaaaggctt tgaaggcctc tctatttgct gacatggtca   1020
gctgggtgcc atgggccaag tccttctgtt gccctcctct gtcaccaagt aagctaggtc   1080 cttctgagg ctcaggtttg ctgtgatgat gatcactttt aggcagaagg ttagaggcct   1140
catgagtgct atatggactt tattaggctt tagatttgat ggggaataag ggatgtgatt   1200
tgtcttttgg gaactcatct ttgattcatc attgtctctt ggtatcttgg aatttccatg   1260
tcattacagt ctacagaatg aaagagtaac ctgtcccaga ggagaggcag gtgaaagact   1320
ccacagcatg ctcattctca ttctgtcttc tcagtgacac cgaggtttac tgagtgccca   1380
ctatgtgcca agcactgtgc tcagggcttt ctttgtatgc atgatctcag tgaatctcac   1440
caagcctcat ctgaaaaacg gggacaaatt aacaacagga tggcaaattg aaaaacacgt   1500
aaccatgttc tacagatgga aagggtgct tggttattat gaaggccccc tcgcaagcgt   1560
gtgggacatg ggtgtgttct ctgggttgta ctgatcagat caaggacctc ccccacccct   1620
ctcacactct gcccacttcc gcccttgct tatcagaccc ttagccagtg actcattcca   1680
gaaccagaac cttggtgaaa tctcaaccga caccagagat cggtgtcttc agtcctagac   1740
tgatggagaa atccagaat atatactaga agctccaaat gctctgggtt tcagctcctc   1800
tgtgctgtgg acactgactt tggctcagaa ctccgattta gtacaaaagg ctcatttta   1860 tttcaggggc actcttccta aagcaaacct aataaatgaa atatggaatt cacagataca   1920
cacacacatt aaaaaattaa cctagtgtat ctgtgaggag taggcagaaa ttcactgtat   1980
aaaagaatgc ttcatttcat agagaatttg tgttaagatt ccattagata gtacatttct   2040
caaagatttt tgaggttgta tttgctttac caaaacttgg tttatgtaag tggaaaaagc   2100
atgttgcaaa ataacttggt gtctatgatt cagtttatgt aaaataataa atgtatgtag   2160
gaatacgtgt gttgaaagat gtacatcaat ttgctaacaa tggttatctc tgacgtggtg   2220
ggatttgaga tgtgttttt ttttggttg tatttttctc tattgtttga cttaacacag   2280
aacatgcttg gttacaacaa taaagttatt gaagacaaaa aaaaaaaaaa aaaaaa      2337
```

<210> SEQ ID NO 14
<211> LENGTH: 6
<212> TYPE: RNA
<213> ORGANISM: Homo sapien

<400> SEQUENCE: 14 gagaac 6

<210> SEQ ID NO 15
<211> LENGTH: 22
<212> TYPE: DNA
<213> ORGANISM: Artificial Sequence
<220> FEATURE:
<223> OTHER INFORMATION: "Scrambled" miR-146a

<400> SEQUENCE: 15
gatcgtgtta atgtgacaat cg 22

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 16
tgcagatctt tgaaaagcca acaggctcat 30

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 17
cagaagcttc cactccaatc ggccctgctg 30

<210> SEQ ID NO 18
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 18
tgccgaggag ggatctagaa accactttcc agagagggtt agcgt 45

<210> SEQ ID NO 19
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 19
acgctaaccc tctctggaaa gtggtttcta gatccctcct cggca 45

<210> SEQ ID NO 20
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 20
agggttagcg tgcagggtgt gcttttggaa taaaagcata tgcaaa 46

<210> SEQ ID NO 21
<211> LENGTH: 46
<212> TYPE: DNA
<213> ORGANISM: Artificial Sequence

```
<220> FEATURE:
<223> OTHER INFORMATION: Oligonucleotide primer

<400> SEQUENCE: 21
tttgcatatg cttttattcc aaaagcacac cctgcacgct aaccct            46

<210> SEQ ID NO 22
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 22
cctagatcta aaatcctttg agctggtctt                              30

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 23
actaagcttt gtccatcctg tccacccttt                              30

<210> SEQ ID NO 24
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 24
ttgaagcttc tggtcttgac ctactgggct c                            31

<210> SEQ ID NO 25
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 25
acaactagtc ctcctttagc ccgagggtgc c                            31

<210> SEQ ID NO 26
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 26
attaagctta gctgaaaact tctggctcac a                            31

<210> SEQ ID NO 27
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 27
ccgacgagtc atgggtagcc ttcggaggga g                            31
```

```
<210> SEQ ID NO 28
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 28
tgtactagta cccatctttc acgcttaaga                              30

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 29
ggtaagcttc tcatcctttg ggatgtacaa                              30

<210> SEQ ID NO 30
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 30
gctgaggact cgtgcaccat gtcttcttct gaccatgaga actttg            46

<210> SEQ ID NO 31
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 31
caaagttctc atggtcagaa gaagacatgg tgcacgagtc ctcagc            46

<210> SEQ ID NO 32
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 32
ccatgtcttc ttctgaccat gtcttctttg acttccggat tggggg            46

<210> SEQ ID NO 33
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 33
ccccaaatcc ggaagtcaaa gaagacatgg tcagaagaag acatgg            46

<210> SEQ ID NO 34
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 34
```
ctataacagg ttaaaaaaat gtcttctcaa ctttctagag caata            45

<210> SEQ ID NO 35
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 35
tattgctcta gaaagttgag aagacatttt tttaacctgt tatag            45

<210> SEQ ID NO 36
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 36
ggaggatccg gaactcctgt ccatttcctt                              30

<210> SEQ ID NO 37
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 37
cctctcgagg aagttgggag cccaaaccat                              30

<210> SEQ ID NO 38
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 38
ctgggatcct aactcatgag tgccaggact                              30

<210> SEQ ID NO 39
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 39
ctgctcgagg agcctgagac tctgccttct                              30

<210> SEQ ID NO 40
<211> LENGTH: 23
<212> TYPE: RNA
<213> ORGANISM: Artificial Sequence
<220> FEATURE:
<223> OTHER INFORMATION: TRAF6-wt miR-146 target site

<400> SEQUENCE: 40
ugcucuagaa aguugaguuc uca                                     23

<210> SEQ ID NO 41
<211> LENGTH: 22
<212> TYPE: RNA
<213> ORGANISM: Artificial Sequence

```
<220> FEATURE:
<223> OTHER INFORMATION: miR-146a

<400> SEQUENCE: 41
uuggguaccu uaagucaaga gu                                              22

<210> SEQ ID NO 42
<211> LENGTH: 23
<212> TYPE: RNA
<213> ORGANISM: Artificial Sequence
<220> FEATURE:
<223> OTHER INFORMATION: TRAF6-mut miR-146 target site

<400> SEQUENCE: 42
ugcucuagaa aguugagaag aca                                             23

<210> SEQ ID NO 43
<211> LENGTH: 28
<212> TYPE: RNA
<213> ORGANISM: Artificial Sequence
<220> FEATURE:
<223> OTHER INFORMATION: IRAK1 ste#1 -wt miR-146a target site

<400> SEQUENCE: 43
cccccaaauc cggaagucaa aguucuca                                        28

<210> SEQ ID NO 44
<211> LENGTH: 28
<212> TYPE: RNA
<213> ORGANISM: Artificial Sequence
<220> FEATURE:
<223> OTHER INFORMATION: IRAK1 site #1 - mut miR-146a target site

<400> SEQUENCE: 44
cccccaaauc cggaagucaa agaagaca                                        28

<210> SEQ ID NO 45
<211> LENGTH: 22
<212> TYPE: RNA
<213> ORGANISM: Artificial Sequence
<220> FEATURE:
<223> OTHER INFORMATION: IRAK1 site #2 - wt miR-146a target site

<400> SEQUENCE: 45
uucucauggu cagaaguucu ca                                              22

<210> SEQ ID NO 46
<211> LENGTH: 22
<212> TYPE: RNA
<213> ORGANISM: Artificial Sequence
<220> FEATURE:
<223> OTHER INFORMATION: IRAK1 site#2 -mut miR-146a target site

<400> SEQUENCE: 46
uucucauggu cagaagaaga ca                                              22
```

MODULATION OF INNATE IMMUNITY RECEPTORS' SIGNALING BY MICRORNAS MIR-146A AND MIR-146B

CROSS-REFERENCE TO RELATED APPLICATIONS

The present application claims priority under 35 U.S.C. § 119(e) to U.S. Provisional Application No. 60/785,394, filed Mar. 23, 2006 which is herein expressly incorporated by reference.

STATEMENT REGARDING FEDERALLY SPONSORED R & D

This invention is funded by Grant No. GM039458 awarded by the National Institutes of Health. The U.S. Government may have certain rights in this invention.

REFERENCE TO SEQUENCE LISTING, TABLE, OR COMPUTER PROGRAM LISTING

The Sequence Listing in electronic format is provided as a file entitled REGLS.002A.TXT, created Jul. 20, 2009, which is 11.0KB in size. The information in the electronic format of the Sequence Listing is incorporated herein by reference in its entirety.

BACKGROUND OF THE INVENTION

1. Field of the Invention

The present application relates to modulating the activity of the innate immune system. More particularly the application relates to modulating innate immune system receptor signaling using microRNA and by inhibiting microRNA activity.

2. Description of the Related Art

Inflammation is a complex, highly regulated defense reaction orchestrated in response to invading pathogen or injury. Inflammation usually proceeds in several sequential stages: it starts with localization of infectious agent, a step that is aimed at preventing of the spread of pathogen to other tissues and organs, and is followed by recognition of the 'danger' signal and activation of the innate immune system and recruitment of specialized immune cells to the site of infection; it ends with the elimination of the pathogen and infected cells by the immune cells of the host, termination of the immune response and repair of damaged tissue. Initiation, smooth transition from one stage to another and especially termination of the inflammatory process is fully dependent on coordinated activities of multiple cell types at the site of inflammation and within the immune system. Ultimately, this coordination is achieved through the ability of cells to communicate with each other through signals in the form of tissue mediators and cytokines.

The initial step of detection of pathogenic organisms invading a host is mediated by the innate immune system. Unlike adaptive immunity, innate immunity does not recognize every possible antigen. Instead, it is designed to recognize a few highly conserved structures present in many different microorganisms. The structures recognized are called pathogen-associated molecular patterns and include, for example, LPS from the gram-negative cell wall, peptidoglycan, lipotechoic acids from the gram-positive cell wall, the sugar mannose (common in microbial glycolipids and glycoproteins but rare in those of humans), bacterial DNA, N-formylmethionine found in bacterial proteins, double-stranded RNA from viruses, and glucans from fungal cell walls. These microbial molecules are sensed by pattern recognition receptors of the Toll/Toll-like receptor (TLR) family, which activate the innate immune response. The binding of a microbial molecule to its TLR transmits a signal to the cell's nucleus inducing the expression of genes coding for the synthesis of intracellular regulatory molecules called cytokines. The cytokines, in turn, bind to cytokine receptors on other defense cells, thus further shaping and enhancing the inflammatory reaction.

Upon binding of their cognate ligands, TLRs recruit adaptor molecules to their intracellular signaling domain, leading to the activation of numerous kinases, activation of several transcriptional factors (e.g. AP-1, NF-kB and IRF3/7), and direct regulation of immune-responsive genes. The TLR signaling cascade starts when an adaptor protein MyD88 is recruited to the receptor complex, followed by its association with the IL-1R-associated kinase 1 (IRAK1). Activated 1RAK1 binds TNF receptor-associated factor (TRAF6), thereby triggering the activation of the downstream effector molecules in the AP-1 and NF-kB activation pathways. NF-kB is a key transcriptional factor that regulates all aspects of the innate immune response from synthesis of pro-inflammatory cytokines such as IL-$\beta$ and TNF$\alpha$ to regulation of immune cell migration to remodeling of the tissues after the successful termination of inflammatory response.

Activation of TLR downstream targets like cytokines TNF and IL-1 can result in a systemic disorder like sepsis or local, chronic inflammation disease like rheumatoid arthritis or inflammatory bowel syndrome. One of the classical modes of regulation of signaling in nature is a transcriptional feedback loop, a mechanism where activation of a certain transcriptional factor leads to a transcriptional activation of a gene that modulates signaling towards activation of this same transcriptional factor. TLRs activate hundreds of genes at the transcriptional level, some of which are secreted molecules that serve as means of communication with other cells, while others are involved in modulation of TLR receptor signaling or mediate crosstalk between TLR receptors and other signaling systems.

MicroRNAs (miRNAs) are a recently discovered class of small RNA molecules that are emerging as potent regulators of multiple aspects of cellular function. MicroRNAs (miRNAs) are evolutionally conserved class of endogenous 22-nucleotide RNAs involved in post-transcriptional gene repression. Bartel, D. P., *Cell* 116, 281-97 (2004); Ambros, V., *Nature* 431, 350-5 (2004); Farh, K. K. et al., *Science* 310, 1817-21 (2005). In animals, miRNAs are processed from larger primary transcripts (pri-miRNA or pri-miR) through an approximate 60-bp hairpin precursor (pre-miRNA or pre-miR) into the mature forms (miRNA) by two RNAse III enzymes, Drosha and Dicer. Gregory, R. I. et al., *Nature* 432, 235-40 (2004); Chendrimada, T. P. et al., *Nature* 436, 740-4 (2005). The mature miRNA is loaded into the ribonucleoprotein complex (RISC), where it typically guides the downregulation of target mRNA through base pair interactions. Pri-miRNAs are transcribed by RNA polymerase II and predicted to be regulated by transcription factors in an inducible manner. Lee, Y. et al., *Embo J* 23, 4051-60 (2004); Fazi, F. et al., *Cell* 123, 819-31 (2005); O'Donnell, K. A., et al., *Nature* 435, 839-43 (2005). While some miRNAs show ubiquitous expression, others exhibit only limited developmental stage-, tissue- or cell type-specific patterns of expression. Pasquinelli et al., *Curr Opin Genet Dev* 15, 200-5 (2005). In mammals, miRNAs have been associated with diverse biological processes, such as cell differentiation (Chen, et al., *Science* 303, 83-6 (2004); Monticelli, S. et al. *Genome Biol* 6, R71 (2005);

Esau, C. et al., *J Biol Chem* 279, 52361-5 (2004)), cancer (Calin, G. A. et al., *Proc Natl Acad Sci USA* 101, 2999-3004 (2004); Lu, J. et al., *Nature* 435, 834-8 (2005); He, L. et al., *Nature* 435, 828-33 (2005)), regulation of insulin secretion (Poy, M. N. et al., *Nature* 432, 226-30 (2004)), and viral infection (Lecellier, C. H. et al., *Science* 308, 557-60 (2005); Sullivan, C. S. and Ganem, D. *Mol Cell* 20, 3-7 (2005)). Studies in plants have shown that miRNAs can be involved in the responses to a variety of environmental stresses.

The human genome contains two miRNA-146 genes with high sequence of homology, miR-146a (Cai, X. et al., *Proc Natl Acad Sci USA* 102, 5570-5 (2005), which is herein expressly incorporated by reference) and miR-146b (Bentwich, I. et al. *Nat Genet* 37, 766-70 (2005), which is herein expressly incorporated by reference). The mature forms of these genes differ only by two nucleotides.

SUMMARY OF THE INVENTION

Immune receptor signaling can be modulated by means of microRNA expression or targeted delivery of said microRNA into the immune cells, and preventing normal microRNA activity, such as by antisense RNA.

Methods for downregulating IL-1 receptor-associated kinase 1 (IRAK1) and TNF receptor-associated factor 6 (TRAF6) expression levels in a target cell are provided in accordance with one aspect of the present invention. In some embodiments, the methods comprise administering a microRNA-146 (miR-146) oligonucleotide to the target cell. In other embodiments, the methods comprise administering a miRNA-146 expression vector to a target cell and expressing a miRNA-146 in the target cell. The miRNA-146 could be, for example, pri-miRNA-146a, pre-miRNA-146a, mature miRNA-146a, pri-miRNA-146b, pre-miRNA-146b, mature miRNA-146b, an oligonucleotide comprising a miRNA-146 seed sequence, or variants thereof. Target cells can be, for example, dendritic cells, macrophages, Th1 helper T cells, Th2 helper T cells, regulator T cells, or any combination thereof.

Methods for upregulating IL-1 receptor-associated kinase 1 (IRAK1) and TNF receptor-associated factor 6 (TRAF6) expression levels in a target cell are provided in accordance with another aspect of the present invention. In some embodiments, the methods comprise administering an antisense microRNA-146 (miR-146) oligonucleotide to the target cell. The antisense miRNA-146 could be, for example, antisense miRNA-146a and/or antisense miRNA-146b. Target cells can be, for example, dendritic cell, a macrophages, Th1 helper T cells, Th2 helper T cells, regulator T cells, or any combination thereof.

Methods for modulating signal transduction from an IL-1 receptor/Toll-like receptor are disclosed in accordance with another aspect of the present invention. In some embodiments, the methods comprise administering a microRNA-146 (miR-146) oligonucleotide directly to a target cell. In other embodiments, the method comprises administering a miRNA-146 expression vector to a target cell and expressing a miRNA-146 in the target cell. In still other embodiments, the methods comprise administering an antisense miR-146 oligonucleotide to a target cell.

Methods for treating disease states associated with activation of innate immune system signaling are provided in accordance with other aspects of the present invention. Diseases may be, for example, sepsis and septic shock, neurodegeneration, neutrophilic alveolitis, asthma, hepatitis, inflammatory bowel disease, ischemia/reperfusion, septic shock, glomerulonephritis, rheumatoid arthritis or Crohn's disease.

In some embodiments, methods comprise administering a miR-146 oligonucleotide, or variants thereof, to a target cell to attenuate signal transduction from an IL-1 receptor/Toll-like receptor, thereby reducing innate immunity signaling.

BRIEF DESCRIPTION OF THE DRAWINGS

FIG. 3 shows that IRAK1 and TRAF6 are targets for miR-146. (*a*) Sequence of the target sites in the 3' UTR of TRAF6 and IRAK1. The mutant sequence (mut) is identical to wild type (wt) construct except for four point substitutions disrupting base pairing with the seed region of miR-146. (*b*) Mutating the miR-146 target site in the TRAF6 and IRAK1 3'-UTRs abolishes inhibition of luciferase activity by miR-146 in transiently transfected 293 cells. Results show relative (n=3) after normalization for β-galactosidase activity.

DETAILED DESCRIPTION OF THE PREFERRED EMBODIMENT

Human microRNA-146a and microRNA-146b gene expression is strongly induced in response to several microbial components that trigger an innate immune response via Toll/Toll-like receptor (TLR) signaling in immune cells, and this activation occurs in an NF-kB-dependent manner. As described in the Examples below, mature 22nt long miR-146 can target and downregulate protein expression level of messenger RNAs of two key adapter molecules, TRAF6 and IRAK, in the TLR and IL-1 receptor signaling cascades and thereby interfere with the signal transduction from these receptors, which play an important role in innate immune signaling. Thus, miR-146 can be used to modulate the innate immune system, for example, as a therapeutic agent to treat disease states characterized by activation, particularly excessive activation of the innate immune system. Such disease states include, for example, sepsis and septic shock, neurodegeneration, neutrophilic alveolitis, asthma, hepatitis, inflammatory bowel disease, ischemia/reperfusion, septic shock, glomerulonephritis, rheumatoid arthritis or Crohn's disease. When miR-146a or miRNA-146b is delivered into cells of the innate immune system, it attenuates signaling of Toll-like and IL-1 receptors and dampens the production of pro-inflammatory cytokines like TNF and IL-1 that cause systemic or chronic, local complications. Such delivery can be achieved in a variety of ways using methods well known in the art, for example, by modification of an oligonucleotide encoding a miR-146, such as a mature miR-146a or miR-146b, with cholesterol to help it easily penetrate the cell membrane or by expressing the miRNA in the cells using an appropriate expression vector. See, for example, Krutzfeldt, J. et al., *Nature* 438, 685-9 (2005), herein expressly incorporated by reference. Delivery of molecules that inhibit miR-146 activity, such as antisense molecules, can be used to upregulate activity of the innate immune system where appropriate.

Figure 1:
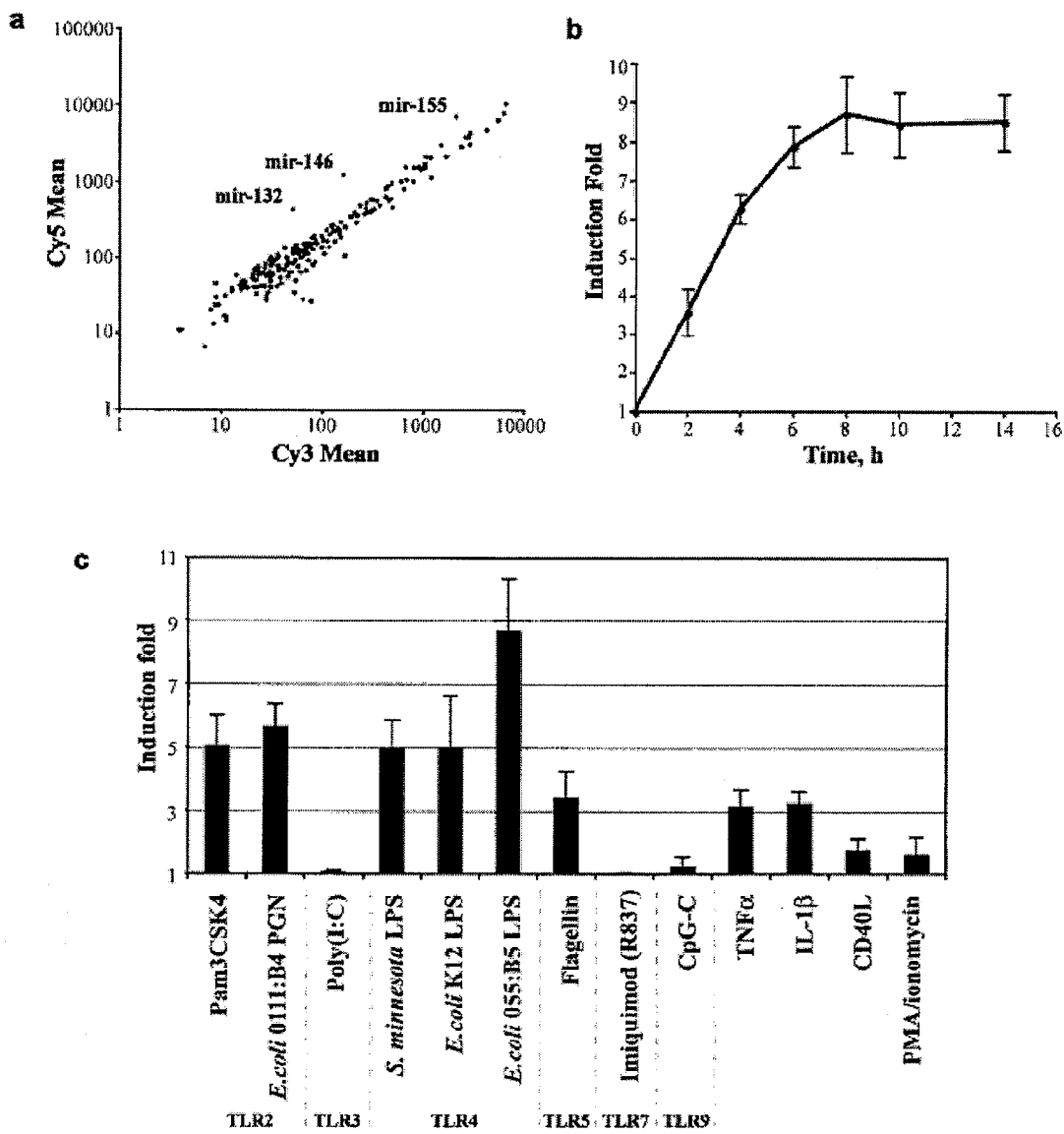
FIG. 1 shows induction of microRNA-146a (miR-146a) and microRNA-146b (miR-146b). (*a*) MiRNA microarray analysis of RNA from THP-1 cells stimulated with LPS. The scatter plot shows background-subtracted raw intensities from each channel for Cy3-labeled control and Cy5-labeled LPS-treated samples. (*b*) THP-1 cells were stimulated with LPS for indicated times, miR-146 levels were analyzed by qPCR and normalized by 5S rRNA expression. (*c*) THP-1 cells were stimulated with the indicated stimuli for 8 h. MiR-146 levels were analyzed by qPCR and normalized by 5s rRNA expression.

The involvement of miR-146a and miR-146b in the innate immune response was identified by screening for microRNAs that are induced by NF-kB activation. MicroRNA gene expression profiling was carried out using human monocytic leukemia cells THP-1 treated with LPS, a strong inducer of NF-kB activation pathway. LPS signals through Toll-like receptor 4 (TLR4) (Poltorak, A. et al. *Science* 282, 2085-8 (1998)), which belongs to a large pattern-recognition receptor family with eleven known members in humans (Takeda, K. et al., *Annu Rev Immunol* 21, 335-76 (2003)). A marked upregulation of expression of miR-146 was seen after LPS challenge and was confirmed by Northern blot analysis and qPCR analysis. Time course experiments revealed that miR-146 is an early response gene that is induced in response to LPS from *E. coli* strain 055:B5 as early as two hours after stimulation and reaches a plateau at around eight hours post stimulation (FIG. 1b).

Human miR-146a is located in the second exon of LOC285628 gene on the human chromosome 5. LOC285628 consists of two exons separated by a long ~16 kb long intron and is most probably a non-coding RNA gene, since it does not contain a long, continuous open reading frame. (FIG. 2a) MiR-146b is located on human chromosome 10.

As described in detail in the examples below, MiR-146a and miR-146b expression was significantly induced by triggering members of the Toll-like receptor family in THP-1 cells. Upregulation of miR-146 gene expression was observed after exposure to PGN (ligand of TLR2), its synthetic analog PAM3CSK4, flagellin (ligand of TLR5), LPS (*E. coli* strain K12 and *S. Minnesota*), TNFα and IL-1β (FIG. 1c).

Three mRNAs coding for proteins known to play a critical role in LPS signaling, namely IRAK1, TRAF6 and COT/Tpl2, were predicted to be targets of miR-146a/b by several microRNA target prediction algorithms (FIG. 3a). (Krek, A. et al. *Nat Genet* 37, 495-500 (2005); Lewis, B. P., et al., *Cell* 115, 787-98 (2003); John, B. et al., *PLoS Biol* 2, e363 (2004); Griffiths-Jones et al., *Acids Res* 34, D140-4 (2006), each of which is herein expressly incorporated by reference). Examples 3 and 4 below show that IRAK1 and TRAF6 are targets for miR-146a and miR-146b. Both IRAK1 and TRAF6 proteins are key adapter molecules in the TLR4-induced NF-kB and AP-1 activation pathways. (Dumitru, C. D. et al., *Cell* 103, 1071-83 (2000)). Thus, miR-146a and/or miR-146b can be used to modulate the innate immune response through interference with Toll-like-receptor signaling.

Definitions

Unless defined otherwise, technical and scientific terms used herein have the same meaning as commonly understood by one of ordinary skill in the art to which this invention belongs. See, e.g. Singleton et al., *Dictionary of Microbiology and Molecular Biology 2nd ed.*, J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

When used herein the terms "miR," "mir" and "miRNA" are used to refer to microRNA, a class of small RNA molecules that are capable of modulating RNA translation (see, Zeng and Cullen, RNA, 9(1):112-123, 2003; Kidner and Martienssen Trends Genet, 19(1):13-6, 2003; Dennis C, Nature, 420(6917):732, 2002; Couzin J, Science 298(5602):2296-7, 2002, each of which is incorporated by reference herein).

"MiRNA-146," "miR-146," "miR-146a/b" and "miRNA-146a/b" which are used interchangeably, refer to microRNA-146a and/or microRNA-146b, including miR-146a, pri-miR-146a, pre-miR-146a, mature miR-146a, miR-146b, pre-miR-146b, mature miR-146b, miRNA-146 seed sequence, sequences comprising a miRNA-146 seed sequence, and variants thereof.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, such as constitutive or inducible promoters.

"MiRNA nucleic acid" is defined as RNA or DNA that encodes a miR as defined above, or is complementary to a nucleic acid sequence encoding a miR, or hybridizes to such RNA or DNA and remains stably bound to it under appropriate stringency conditions. Specifically included are genomic DNA, cDNA, mRNA, miRNA and antisense molecules, pri-miRNA, pre-miRNA, mature miRNA, miRNA seed sequence, as well as nucleic acids based on alternative backbones or including alternative bases. MiRNA nucleic acids can be derived from natural sources or synthesized.

"MicroRNA seed sequence," "miRNA seed sequence," "seed region" and "seed portion" are used to refer to nucleotides 2-7 or 2-8 of the mature miRNA sequence. The miRNA seed sequence is typically located at the 5' end of the miRNA. A miRNA-146 seed sequence is provided in SEQ ID NO: 14.

An "antisense miR," "anti-miRNA," or "anti-miR" is an nucleic acid molecule comprising or consisting of a sequence that is complementary to that of a particular miRNA. Preferred antisense miR molecules can inhibit miRNA function.

The term "operably linked" is used to describe the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

The term "mammal" is defined as an individual belonging to the class Mammalia and includes, without limitation, humans, domestic and farm animals, and zoo, sports, or pet animals, such as sheep, dogs, horses, cats or cows. Preferably, the mammal herein is human. However, in some embodiments the mammal is not a human.

As used herein, "treatment" is a clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Those in need of treatment include those already affected by a disease or disorder or undesired physiological condition as well as those in which the disease or disorder or undesired physiological condition is to be prevented.

The term "effective amount" refers to an amount sufficient to effect beneficial or desirable biological and/or clinical results.

"Pharmaceutically acceptable" carriers, excipients, or stabilizers are ones which are nontoxic to the cell or mammal being exposed thereto at the dosages and concentrations employed or that have an acceptable level of toxicity as determined by the skilled practitioner. Often the physiologically acceptable carrier is an aqueous pH buffered solution. The physiologically acceptable carrier may also comprise one or more of the following: antioxidants, such as ascorbic acid, low molecular weight (less than about 10 residues) polypeptides, proteins, such as serum albumin, gelatin, immunoglobulins, hydrophilic polymers such as polyvinylpyrrolidone, amino acids, carbohydrates such as glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™.

MiR-146 Nucleic Acid Molecules

Nucleic acid molecules that encode miR-146 are used in various embodiments of the present invention. miR-146 sequences for mature miR-146a, pre-miR-146a, mature miR-146b and pre-miR-146b are provided in SEQ ID NOs: 1, 2, 3 and 4, respectively. cDNAs encoding mature miR-146a, pre-miR-146a, mature miR-146b and pre-miR-146b, are provided in SEQ ID NOs: 5, 6, 7 and 8, respectively. Nucleic acid molecules encoding pri-miR-146a and pri-miR-146b sequences can also be used in accordance with some embodiments.

A miRNA sequence may comprise from about 6 to about 99 or more nucleotides. In some embodiments, a miRNA sequence comprises about the first 6 to about the first 22 nucleotides of a pre-miRNA-146. Isolated or purified polynucleotides having at least 6 nucleotides (i.e., a hybridizable portion) of a miR-146 coding sequence or its complement are used in some embodiments. In other embodiments, miR-146 polynucleotides preferably comprise at least 22 (continuous) nucleotides, or a full-length miR-146 coding sequence. In preferred embodiments a miR-146 sequence comprises at least a miR-146 seed sequence, such as that provided in SEQ ID NO: 14.

In some embodiments, a miRNA-146 sequence comprises nucleotides 2-7 of mature miRNA-146. In other embodiments, a miRNA-146 comprises a miRNA-146 seed sequence having the sequence of SEQ ID NO: 14 or a sequence complementary to the miRNA-146 seed sequence of SEQ ID NO: 14.

In still other embodiments, the miRNA sequence comprises a miRNA-146 seed sequence fusion molecule comprising SEQ ID NO: 14.

Nucleotide sequences which encode a miR-146, such as a pre-miR-146, mature miR-146 or nucleic acid comprising a miR-146 seed sequence, or a fusion molecule comprising any of the foregoing, can be used to generate recombinant molecules which direct the expression of the miRNA-146 in a target cell, as described in more detail below.

In some embodiments, nucleic acids are used that are capable of blocking the activity of a miRNA. Such nucleic acids include, for example, antisense miR (anti-miRNA or anti-miR). In preferred embodiments, the anti-miR is an anti-miRNA nucleic acid comprising a total of about 5 to about 100 or more, more preferably about 10 to about 60 nucleotides, and has a sequence that is preferably complementary to at least the seed region of miR-146. In particularly preferred embodiments, an anti-miRNA may comprise a total of at least about 5, to about 26 nucleotides. In some embodiments, the sequence of the anti-miRNA can comprise at least 5 nucleotides that are substantially complementary to the 5' region of a miR-146, at least 5 nucleotides that are substantially complementary to the 3' region of a miR-146, at least 4-7 nucleotides that are substantially complementary to a miR-146 seed sequence, or at least 5-12 nucleotide that are substantially complementary to the flanking regions of a miR-146 seed sequence.

In some embodiments, an anti-miRNA comprises the complement of a sequence of a miRNA referred to in SEQ ID NOs: 1-4. Preferred molecules are those that are able to hybridize under stringent conditions to the complement of a cDNA encoding a mature miR-146, for example SEQ ID NO: 1 or SEQ ID NO: 3. Particular antisense sequences for miR-146a and miR-146b are provided in SEQ ID NOs: 9 and 10.

It is not intended that the methods of the present invention be limited by the source of the miR-146 or anti-miR-146. Human and mouse synthetic miR-146a and miR-146b are commercially available, as are inhibitors thereof. For example, both miRNA precursors and miRNA inhibitors for miR-146a and miR-146b can be purchased from Ambion®. It has been shown that antisense miRNAs can specifically silence target miRNA in tissue. Krutzfeldt, J. et al., Nature 438, 685-9 (2005).

The miR-146 can be from a human or non-human mammal, derived from any recombinant source, synthesized in vitro or by chemical synthesis. The nucleotide may be DNA or RNA and may exist in a double-stranded, single-stranded or partially double-stranded form, depending on the particular context. miR-146 and anti-miR-146 nucleic acids may be prepared by any conventional means typically used to prepare nucleic acids in large quantity. For example, nucleic acids may be chemically synthesized using commercially available reagents and synthesizers by methods that are well-known in the art for example, the phosphotriester method of Matteucci, et al., (J. Am. Chem. Soc. 103:3185-3191, 1981) and/or using automated synthesis methods. (See, e.g., Gait, 1985, Oligonucleotide Synthesis: A Practical Approach, IRL Press, Oxford, England). In addition, larger DNA or RNA segments can readily be prepared by well known methods, such as synthesis of a group of oligonucleotides that define various modular segments, followed by ligation of oligonucleotides to build the complete segment.

Nucleotide sequences that encode a mutant of a miR-146 that is a miR-146a/b with one or more substitutions, additions and/or deletions, and fragments of miR-146, as well as truncated forms of miR-146 may also be useful in the methods of the present invention.

To increase stability or optimize delivery of sense or antisense oligonucleotides, modified nucleotides or backbone modifications can be utilized. For example, modified nucleotides may include: linked nuclear acid (LNA), 2'-O-Me nucleotides, 2'-O-methoxyethyl, and 2'-fluoro. Backbone modifications include, for example, phosphorothioate and phosphate.

In some embodiments, a miR-146 or anti-miR-146 oligonucleotide is modified with cholesterol to enhance delivery to the target cell. The cholesterol can be linked, for example, through a hydroxyprolinol linkage on the 3' end of the miRNA.

Nucleic acid molecules encoding miR-146 (i.e., synthetic oligonucleotides) are used in some embodiments of the present invention, for example, to downregulate IRAK1 and/or TRAF6 expression levels in a target cell, upregulate IRAK1 and TRAF6 expression levels in a target cell, to modulate signal transduction from an IL-1 receptor/Toll-like receptor, to modulate the activity of the innate immune system and/or to treat a disease state characterized by activation or suppression of innate immunity signaling.

MiR-146 Expression Vectors

Expression vectors that contain a miR-146 or anti-miR-146 coding sequence are also useful in the present invention for delivery of a miR-146 or anti-miR146 to target cells. Thus the present invention also contemplates expression vectors that contain a miR-146 sequence and/or anti-miR-146, optionally associated with a regulatory element that directs the expression of the coding sequences in a target cell. MiR-146 sequences are described in detail in the previous section. The choice of vector and/or expression control sequences to which the encoding sequence is operably linked depends directly, as is well known in the art, on the functional properties desired, e.g., miRNA transcription, and the host cell to be transformed.

A vector contemplated by the present invention is preferably capable of directing replication in an appropriate host and of expression of a miR-146 or anti-miR-146 included in a target cell. Vectors that can be used are well known in the art and include, but are not limited to, pUC8, pUC9, pBR322 and pBR329 available from BioRad Laboratories, (Richmond, Calif.), pPL and pKK223 available from Pharmacia (Piscataway, N.J.) for use in prokaryotic cells, and pSVL and pKSV-10 (Pharmacia), pBPV-1/pML2d (International Biotechnologies, Inc.), pCDNA and pTDT1 (ATCC, #31255), for use in eukaryotic cells, as well as eukaryotic viral vectors such as adenoviral or retroviral vectors.

Vectors may include a selection gene whose expression confers a detectable marker such as a drug resistance. Typical selection genes encode proteins that confer resistance to antibiotics or other toxins, e.g., ampicillin, neomycin, methotrexate, or tetracycline, complement auxotrophic deficiencies, or supply critical nutrients withheld from the media. Such selection systems are well known in the art. The selectable marker can optionally be present on a separate plasmid and introduced by co-transfection.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium. In some embodiments, the promoter is the U6 promoter or CMV promoter.

Other methods, vectors, and host cells suitable for adaptation to the synthesis of a miR-146 in recombinant vertebrate cell culture and the expression of miR-146 in target cells are well known in the art and are readily adapted to the specific circumstances.

Delivery of Oligonucleotides and Expression Vectors to a Target Cell

In some embodiments, a miR-146 or anti-miR-146 oligonucleotide is delivered to a target cell. In other embodiments, an expression vector encoding a miR-146 or anti-miR-146 is delivered to a target cell where the miR-146 or anti-miR-146 is expressed. Methods for delivery of oligonucleotides and expression vectors to target cells are well known in the art and are described briefly below. Target cells can be any cell type involved in innate immunity. Target cells include, for example, dendritic cells, macrophages, helper T cells such as $T_{h1}$ and $T_{h2}$ cells, regulator T cells ($T_{reg}$), and combinations thereof.

Delivery of oligonucleotides and/or expression vectors to a target cell can be achieved in a variety of ways. In some embodiments, a transfection agent is used. A transfection agent, or transfection reagent or delivery vehicle, is a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, polycations, histone proteins, polyethylenimine, polylysine, and polyampholyte complexes. Transfection reagents are well known in the art. One transfection reagent suitable for delivery of miRNA is siPORT™ NeoFX™ transfection agent (Ambion), which can be used to transfect a variety of cell types with miRNA. miRNAs can be readily electroporated into primary cells without inducing significant cell death. In addition, miRNAs can be transfected at different concentrations. The transfection efficiency of synthetic miRNAs has been shown to be very good, and around 100% for certain cell types (Ambion.RTM. miRNA Research Guide, page 12. See also, the world wide web address Ambion.com/miRNA.

Reagents for delivery of miRNA, anti-miRNA and expression vectors can include, but are not limited to protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups can include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers). For delivery in vivo, complexes made with sub-neutralizing amounts of cationic transfection agent may be preferred.

In some embodiments, polycations are mixed with polynucleotides for delivery to a cell. Polycations are a very convenient linker for attaching specific receptors to DNA and as result, DNA/polycation complexes can be targeted to specific cell types. Here, targeting is preferably to cells involved in innate immunity. An endocytic step in the intracellular uptake of DNA/polycation complexes is suggested by results in which functional DNA delivery is increased by incorporating endosome disruptive capability into the polycation transfection vehicle. Polycations also cause DNA condensation.

The volume which one DNA molecule occupies in complex with polycations is drastically lower than the volume of a free DNA molecule. The size of DNA/polymer complex may be important for gene delivery in vivo. In some embodiments, miR-146 or anti-miR-146 nucleic acids and a transfection reagent are delivered systematically such as by injection. In other embodiments, they may be injected into particular areas comprising target cells.

Polymer reagents for delivery of miRNA, anti-miRNA and expression vectors may incorporate compounds that increase their utility. These groups can be incorporated into monomers prior to polymer formation or attached to polymers after their formation. A miRNA, anti-miRNA or expression vector transfer enhancing moiety is typically a molecule that modifies a nucleic acid complex and can direct it to a cell location (such as tissue cells) or location in a cell (such as the nucleus) either in culture or in a whole organism. By modifying the cellular or tissue location of the complex, the desired localization and activity of the miRNA, anti-miRNA or expression vector can be enhanced. The transfer enhancing moiety can be, for example, a protein, peptide, lipid, steroid, sugar, carbohydrate, nucleic acid, cell receptor ligand, or synthetic compound. The transfer enhancing moieties can enhance cellular binding to receptors, cytoplasmic transport to the nucleus and nuclear entry or release from endosomes or other intracellular vesicles.

Nuclear localizing signals can also be used to enhance the targeting of the miRNA, anti-miRNA or expression vector into proximity of the nucleus and/or its entry into the nucleus. Such nuclear transport signals can be a protein or a peptide such as the SV40 large Tag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Compounds that enhance release from intracellular compartments can cause DNA release from intracellular compartments such as endosomes (early and late), lysosomes, phagosomes, vesicle, endoplasmic reticulum, Golgi apparatus, trans Golgi network (TGN), and sarcoplasmic reticulum and could be used to aid delivery of miRNA-146 or anti-miR-146. Release includes movement out of an intracellular compartment into cytoplasm or into an organelle such as the nucleus. Such compounds include chemicals such as chloroquine, bafilomycin or Brefeldin Al and the ER-retaining signal (KDEL sequence), viral components such as influenza virus hemagglutinin subunit HA-2 peptides and other types of amphipathic peptides.

Cellular receptor moieties are any signal that enhances the association of the miRNA, anti-miRNA or expression vector with a cell. Enhanced cellular association can be accomplished by either increasing the binding of the polynucleotide or polynucleotide complex to the cell surface and/or its association with an intracellular compartment, for example: ligands that enhance endocytosis by enhancing binding the cell surface. Cellular receptor moieties include agents that target to asialoglycoprotein receptors by using asialoglycoproteins or galactose residues. Other proteins such as insulin, EGF, or transferrin can be used for targeting. Peptides that include the RGD sequence can also be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to target cells.

The skilled artisan will be able to select and use an appropriate system for delivering miRNA-146, anti-miRNA-146 or an expression vector to target cells without undue experimentation.

Modulation of IRAK1 and TRAF6 Expression in Target Cells

Protein expression levels of IRAK1 and TRAF6 can be modulated by modulating levels of miR-146 in target cells. Upregulation of miRNA-146 in target cells can be accomplished by, for example, administering to the cells either synthetic miRNA-146, such as a miR-146 oligonucleotide, or expression vectors that express miRNA-146. Downregulation of miRNA-146 in cells can be accomplished by, for example, administering to the cells either synthetic antisense miRNA-146 or expression vectors that express antisense miRNA-146.

Target cells may be any cells which are active in innate immunity signaling. Preferably, target cells include one or more of dendritic cells, macrophages, T1 helper T cells, T2 helper T cells and regulator T cells.

In some embodiments, to downregulate IRAK1 and TRAF6 expression levels in a target cell, a miR-146 oligonucleotide or miR-146 expression vector is administered to the cell. The miR-146 oligonucleotide or expression vector can be administered to the cells, for example, by transfection. Methods for transfection are described generally above and are well-known in the art. In some embodiments, the miR-146 oligonucleotide comprises mature miR-146a, mature miR-146b, pre-miR-146a, pre-miR-146b, pri-miR-146a, pri-miR-146b, or a miR-146 seed sequence. Mixtures of various miR-146 nucleic acids can also be used. In some embodiments, the miR-146 comprises a sequence selected from the group consisting of SEQ ID NO: 1, SEQ ID NO: 2, SEQ ID NO: 3, SEQ I) NO: 4 or SEQ ID NO: 14. In some embodiments, the miR-146 expression vector comprises a sequence encoding a miRNA-146 selected from the group consisting of SEQ ID NO: 5, SEQ ID NO: 6, SEQ ID NO: 7 or SEQ ID NO: 8. After transfection, the miR-146 is expressed in the cell.

In some embodiments, the miR-146 expression vector comprises a nucleic acid sequence encoding a miRNA-146 operably linked to a U6 promoter or a CMV promoter.

In some embodiments, to upregulate IRAK1 and TRAF6 expression levels in a target cell, an antisense miR-146 oligonucleotide or antisense miR-146 expression vector is administered to the cell. In some embodiments, the antisense miR-146 comprises SEQ ID NO: 9 or SEQ ID NO: 10.

The miR-146 may be modified to enhance delivery. For example, in some embodiments, the miR-146 oligonucleotide is modified with cholesterol. In other embodiments, the miR-146 oligonucleotide comprises modification such as a linked nuclear acid (LNA), 2'-O-Me nucleotides, 2'-O-methoxyethyl, and 2'-fluoro, phosphorothioate or phosphate.

Modulation of Signal Transduction From an IL-1 Receptor/Toll-like Receptor

Signal transduction from an IL-1 receptor or Toll-like receptor can be modulated by modulating levels of miR-146 in target cells. Upregulation of miRNA-146 and thus downregulation of signal transduction in target cells can be accomplished by, for example, administering to the cells either synthetic miRNA-146, such as a miR-146 oligonucleotide, or expression vectors that express miRNA-146. Downregulation of miRNA-146 and thus upregulation of signal transduction in target cells can be accomplished by, for example, administering to the cells either anti-miRNA-146 or expression vectors that express anti-miRNA-146.

In some embodiments, to modulate signal transduction from an IL-1 receptor or Toll-like receptor in a target cell, a miR-146 oligonucleotide or miR-146 expression vector is administered to the cell. The miR-146 oligonucleotide or expression vector can be administered to the cells by transfection. Methods for transfection are described generally above and are well known in the art. In some embodiments, the miR-146 is comprises mature miR-146a, mature miR-146b, pre-miR-146a, pre-miR-146b, pri-miR-146a, pri-miR-146b, or miR-146 seed sequence. In some embodiments, the miR-146 comprises a sequence selected from the group consisting of SEQ ID NO: 1, SEQ ID NO: 2, SEQ ID NO: 3, SEQ ID NO: 4 or SEQ ID NO: 14. In some embodiments, the miR-146 expression vector comprises a sequence encoding a miRNA-146 selected from the group consisting of SEQ ID NO: 5, SEQ ID NO: 6, SEQ ID NO: 7 or SEQ ID NO: 8.

In some embodiments, the miR-146 expression vector comprises a nucleic acid sequence encoding a miRNA-146 operably linked to a U6 promoter or a CMV promoter.

In some embodiments, the signal transduction from an IL-1 receptor or Toll-like receptor is attenuated in providing miR-146 oligonucleotides to a target cell or by expressing miR-146 in a target cell. The IL-1 receptor or Toll-like receptor can be IL-1 receptor, Toll-like receptor 4, (TLR4), Toll-like receptor 2, (TLR2) or Toll-like receptor 5, (TLR5).

In some embodiments, the production of at least one pro-inflammatory cytokine is dampened by providing a miR-146 nucleic acid to a target cell. In some embodiments, the production of TNF or IL-1 is dampened.

In some embodiments, the expression level of at least one adapter molecule is downregulated by providing miR-146 to a target cell. In some embodiments, the expression level of IRAK1 or TRAF6 is downregulated.

The following Examples are offered by way of illustration and not by way of limitation.

EXAMPLE 1

MicroRNA-146a and MicroRNA-146b are Induced By LPS Stimulation

To screen for microRNAs that are potentially induced by NF-kB activation, microRNA gene expression profiling was carried out using human monocytic leukemia cells THP-1 treated with LPS, a strong inducer of NF-kB activation pathway. THP-1 cells were stimulated with 1 ug/mL LPS for 8 h and their total RNA was isolated using the mirVana® RNA Isolation kit (Ambion). Forty micrograms of total RNA were enriched for small RNA species, tailed (mirVana® miRNA Labeling kit, Ambion) and fluorescently labeled using an amine-reactive Cy3 and Cy5 (Amersham). The fluorescently labeled RNA from control and LPS treated cells were mixed. Each sample mixture was hybridized for 14 hr with epoxy-coated slides (Nexterion) upon which 200 miRNA probes were arrayed in quadruplicate (mirVana® miRNA Probe Set, Ambion). The microarray were washed as recommended by manufacturer and scanned using a GenePix 4000® microarray scanner.

Figure 2:
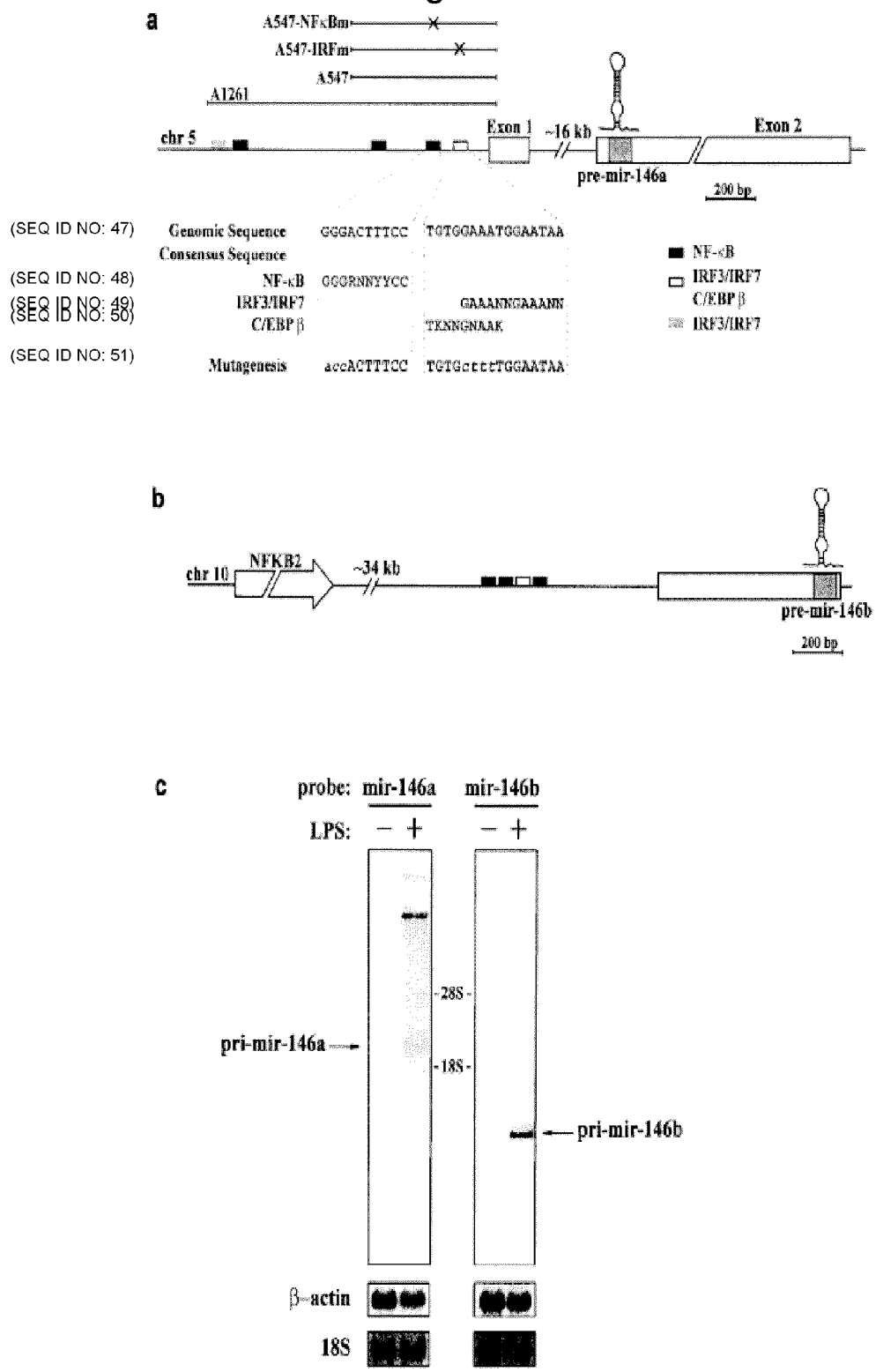
FIG. 2 shows mutational analysis of miR-146a and miR-146b promoters. (*a*) and (*b*) A schematic representation of miR-146a and miR-146b localization on chromosome 5 and 10, respectively. (*c*) Northern blot analysis of miR-146a/b transcripts in THP-1 cells after 8 h of LPS stimulation.

Northern blot analysis of pre-miR-146 expression in LPS stimulated THP-1 cells with probes corresponding to pre-miR-146a and pre-miR-146b, respectively, was carried out. In the case of pre-miR-146b, a single, relatively small (~750 bp) band was observed upon 8 hour LPS stimulation. The pri-miR-146a probe recognized two bands (more than 10 kb and approximately 2.3 kb) in LPS-treated sample (FIG. 2c). The 3'- and 5'-RACE (rapid amplification of cDNA ends) technique was used to characterize transcripts of both human mir146a and miR-146b. Their sizes exactly matched the bands observed on Northern blots with pre-miR-146a and b, respectively. (FIG. 2b).

Reagents and Antibodies

THP-1, U937, HL-60 and Ramos were from ATCC. PGN (*E. coli* strain 0111 :B4), CpG oligonucleotide type C, synthetic bacterial lipoprotein Pam3CSK4, ultra pure LPS (*S. Minnesota* and *E. coli* strain K12), poly(l:C), recombinant flagellin (*S. typhimurium*), imiquimod-R837 were from Invitrogen. LPS (*E. coli* 055:B5) was from Sigma; PMA from Sigma; ionomycin from Calbiochem. Recombinant human proteins were purchased: IL-1β (Cell Sciences), CD-40L (R&D systems), TNFα (Biosource International).

Cell Culture, Stimulations, RNA Isolation and MlRNA Quantitative PCR

THP-1, U937, HL-60, Bjab and Ramos cells were grown in RPMI1640 media supplemented with 10% FBS, 1× nonessential amino acids, 100 g/ml of penicillin and streptomycin, and 2 mM glutamine in a 37° C. incubator with 5% humidified $CO_2$. 293 IL-1 R/MD2/TLR4 cells were grown in DMEM supplemented with 10% FBS, 100 g/ml of penicillin and streptomycin, and 2 mM glutamine. Twenty-four hours before stimulation, 1 million cells was seeded in RPMI1640 media containing 0.5% FBS. The cells were stimulated for 8 h with final concentrations as follows: 100 ng/mL LPS (*E. coli* 055:B5), 100 ng/mL Pam3CSK4, 10 ug/mL PGN, 5 uM CpG oligonucleotide type C, 10 ug/mL ultra pure LPS (*S. Minnesota* and *E. coli* strain K12), 25 ug/mL poly(l:C), 100 ng/mL recombinant flagellin (*S. typhimurium*), 5 ug/mL imiquimod-R837, 10 ng/mL TNFa, 10 ng/mL IL-1β, 300 ng/mL CD-40L, 50 ng/mL PMA in combination with 1 uM ionomycin. Total RNA was isolated using mirVana miRNA Isolation kit (Ambion). miRNA expression was measured with MirVana qRT-PCR miRNA Detection Kit (Ambion) according to specified protocol and normalized by 5S rRNA levels.

RNA Isolation and Gene Expression Analysis

Total RNA was isolated using a QIAGEN RNeasy® kit with on-column DNAse digestion, according to manufacturer's instructions, and hybridized to Affymetrix GeneChip® Human Genome 133 Plus 2.0 array, according to specified protocols. Rosetta Resolver® software (Rosetta Biosoftware) was used to normalize and analyze the chip data. PCR was performed using SYBR® Green PCR Master Mix (Applied Biosystem®) and an Applied Biosystems® Real-Time PCR machine according to manufacturer's instructions. β-actin transcript was used to normalize between samples. Primer sequences are set forth in the following table. Non-template nucleotides (incorporated restriction endonuclease sites or directed mutagenesis) are shown in lowercase.

| Construct name | Primers used for construction | |
|---|---|---|
| A547 | TGCagatctTTGAAAAGCCAACAGGCTCAT | (SEQ ID NO: 16) |
| | CAGaagcttCCACTCCAATCGGCCCTGCTG | (SEQ ID NO: 17) |
| A547_NFκBm | TGCCGAGGAGGGATCTAGAAaccACTTTCCAGAGAGGGTTAGCGT | (SEQ ID NO: 18) |
| | ACGCTAACCCTCTCTGGAAAGTggtTTCTAGATCCCTCCTCGGCA | (SEQ ID NO: 19) |
| A547_IRFm | AGGGTTAGCGTGCAGGGTGTGctttTGGAATAAAAGCATATGCAAA | (SEQ ID NO: 20) |
| | TTTGCATATGCTTTTATTCCAaaagCACACCCTGCACGCTAACCCT | (SEQ ID NO: 21) |
| A1261 | CCTagatctAAAATCCTTTGAGCTGGTCTT | (SEQ ID NO: 22) |
| | ACTaagcttTGTCCATCCTGTCCACCCTTT | (SEQ ID NO: 23) |
| IRAK1-UTR | TTGaagcttCTGGTCTTGACCTACTGGGCTC | (SEQ ID NO: 24) |
| | ACAactagtCCTCCTTTAGCCCGAGGGTGCC | (SEQ ID NO: 25) |
| TRAF6-UTR | ATTaagcttAGCTGAAAACTTCTGGCTCACA | (SEQ ID NO: 26) |
| | CCGacgcgtCATGGGTAGCCTTCGGAGGGAG | (SEQ ID NO: 27) |
| COT_UTR | TGTactagtACCCATCTTTCACGCTTAAGA | (SEQ ID NO: 28) |
| | GGTaagcttCTCATCCTTTGGGATGTACAA | (SEQ ID NO: 29) |
| IRAK1-UTRm | GCTGAGGACTCGTGCACCATGtcttCTTCTGACCATGAGAACTTTG | (SEQ ID NO: 30) |
| | CAAAGTTCTCATGGTCAGAAGaagaCATGGTGCACGAGTCCTCAGC | (SEQ ID NO: 31) |
| | CCATGtcttCTTCTGACCATGtcttCTTTGACTTCCGGATTTGGGG | (SEQ ID NO: 32) |
| | CCCCAAATCCGGAAGTCAAAGaagaCATGGTCAGAAGaagaCATGG | (SEQ ID NO: 33) |
| TRAF6-UTRm | CTATAACAGGTTAAAAAAATGtcttCTCAACTTTCTAGAGCAATA | (SEQ ID NO: 34) |
| | TATTGCTCTAGAAAGTTGAGaagaCATTTTTTTAACCTGTTATAG | (SEQ ID NO: 35) |
| cmv-146B | GGAggatccGGAACTCCTGTCCATTTCCTT | (SEQ ID NO: 36) |
| | CCTctcgagGAAGTTGGGAGCCCAAACCAT | (SEQ ID NO: 37) |
| cmv-146A | CTGggatccTAACTCATGAGTGCCAGGACT | (SEQ ID NO: 38) |
| | CTGctcgagGAGCCTGAGACTCTGCCTTCT | (SEQ ID NO: 39) |

Northern Blot Analysis

Twenty-four hours before stimulation cells were seeded in RPMI1640 media containing 0.5% FBS. Cells were stimulated for 8 h and RNA was isolated using either mirVana™ miRNA Isolation kit (Ambion) or TRI-reagent (Molecular Research Center). For detection of mature miRNA species 30 ug of total RNA were loaded on 12% polyacrylamide denaturing gel along with [γ-$^{32}$P]-labeled Decade™ Marker (Ambion) and transferred on GeneScreen Plus® (Perkin Elmer) membrane by electro transfer (BioRad). Hybridizations were performed in ULTRAhyb®-Oligo (Ambion) as recommended by manufacturer using [γ-$^{32}$P]-labeled probes complimentary to mature miRNAs. For pri-miR-146a/b detection 15 ug of total RNA were loaded on formaldehyde containing 1.2% agarose gel and transferred on GeneScreen Plus® membrane by capillary transfer. Hybridizations were performed in ULTRAhyb® (Ambion). DNA fragments (~300 bp) containing pre-miR-146a or pre-miR-146b were amplified from human genomic DNA, [α-$^{32}$P]-labeled and used as probes.

EXAMPLE 2

NF-kB Activates MiR-146a Transcription

A Genomatix™ MatInspector™ software package (available at the world wide web address genomatix.de) was used to identify putative transcription factor binding sites in respective miR-146a and b promoters. The transcription factors involved in TLR, IL-1.beta. and/or TNF.alpha. signaling were the primary area of focus. Scanning of the 1500 by region upstream of LOC285628 exon 1 resulted in identification of three putative NF-kB binding sites (Ghosh, S. et al., "NF-kappa B and Rel proteins: evolutionarily conserved mediators of immune responses," Annu Rev Immunol 16, 225-60 (1998) and two IRF3/IRF7 site (Lin, et al., "Selective DNA binding and association with the CREB binding protein coactivator contribute to differential activation of alpha/beta interferon genes by interferon regulatory factors 3 and 7," Mol Cell Biol 20, 6342-53 (2000)), one of which is overlapping with C/EB-P.beta. (NF-IL6) site (Akira, S. et al., "A nuclear factor for IL-6 expression (NF-IL6) is a member of a CIEBP family," Embo J 9, 1897-906 (1990)). A similar analysis for miR-146b promoter resulted in the 600 by upstream of the transcript start site.

A number of constructs encompassing a portion of microRNA promoter that contains several putative NF-kB sites fused to the firefly luciferase gene (FIG. 2b, c) were tested for activation by LPS, TNF and IL1 in 293IL-1 R/TLR4/MD2 cells (Qin, J. "SIGIRR inhibits interleukin-1 receptor- and toll-like receptor 4-mediated signaling through different mechanisms," J Biol Chem 280, 25233-41 (2005)). In case of miR-146a, both a long and a short promoter constructs (A1261 and A547) showed similar, strong induction (6-7 fold activation) upon LPS and IL-1β treatment, and were moderately (3 fold) induced by TNFα, suggesting that A547 promoter constructs contains all sufficient regulatory elements for LPS activation and the region upstream does not contribute to the regulation.

Two constructs with mutations in either one of the NF-kB sites (A547-NF-k Bm) or in IRF3/IRF7/C/EBPβ site (A547-IRFm) were generated to examine the role of the putative transcription factor binding sites in miR-146a regulation. While constructs A547 and A547-IRFm show very similar LPS-, IL-1β- and TNFα-induced luciferase activity, the mutation of the NF-kB site abolished the stimulation of the miR-146a promoter by all stimuli tested, suggesting that miR-146a induction is an NF-kB-dependent gene.

EXAMPLE 3

MiR-146a/b Downregulate Expression Levels of IRAK1 and TRAF6 mRNA

Luciferase constructs were used to test whether IRAK1, TRAF6 and COT/TpI2 are in fact targets of miR-146a/b. ~700 bp taken from 3'-UTRs of mRNAs coding for IRAK1, TRAF6 and COT1 and encompassing putative miR-146 binding sites were cloned downstream of firefly luciferase gene (IRAK1-UTR, TRAF6-UTR and COTI-UTR, respectively). These luciferase constructs were co-expressed with miR-146a/b expression constructs in 293T cells and the effect of miR-146 expression was assessed in a luciferase reporter assay.

Mutating the miR-146a/b target site in the TRAF6 and IRAK1 3'-UTRs abolishes inhibition of luciferase activity by miR-146 in transiently transfected 293 cells. Results show relative (n=3) after normalization for .beta.-galactosidase activity. FIG. 3a depicts the sequence of the target sites in the 3' UTR of TRAF6 and IRAK1 (SEQ ID NOs: 40, 42, and 45, respectively). The mutant sequences (mut)(SEQ ID NOs: 42, 44 and 46), are identical to the corresponding wild type (wt) constructs except for four point substitutions disrupting base pairing with the seed region of miR-146 (shown as SEQ ID NO: 41).

As shown in FIGS. 3b and c, IRAK1-UTR and TRAF6-UTR showed three-fold reduction in luciferase expression when co-expressed with CMV-driven pre-miR-146a or pre-miR-146b (cmv-146a and cmv-146b), suggesting that indeed TRAF6 and IRAK1 mRNAs are targets for regulation by miR-146a/b. In contrast, no significant changes in luciferase expression levels in similar experiment with COT1-UTR were observed.

FIG. 3b and c show results of a luciferase reporter assay demonstrating that point mutations introduced into the predicted miR-146 binding sites of IRAKI-UTR and TRAF6-UTR completely abolish the ability of miR-146 to repress IRAK1-UTR and TRAF6-UTR expression. These results demonstrate that IRAK1 and TRAF6 are targets for miR-146a and miR-146b. Thus, miR-146 expression or targeted delivery into the cells can modulate Toll-like-receptor signaling.

Constructs and Luciferase Reporter Assays

293 IL-I R/TLR4/MD2 cells were plated at $10^5$ cells per well in 24-well dishes and were transfected 24 hr later by the calcium phosphate method. Each transfection contained 100 ng of pGL3 vector with miR-146a/b promoter fragment and 200 ng of pcDNA3 (carrier). For normalization of transfection efficiency and extract recovery, the transfection included the pCSK-lacZ vector (40 ng), which constitutively expresses β-galactosidase and is unaffected by NF-kB. Luciferase and β-galactosidase activities were measured as described elsewhere (Pomerantz, et al., "CARD11 mediates factor-specific activation of NF-kappaB by the T cell receptor complex," *Embo J* 21, 5184-94 (2002)).

Wild-type and mutant UTR segments of IRAKI, TRAF6 and COT1 genes were cloned into the 3' UTR of CMV-driven Firefly® Luciferase gene (pMIR-REPORT, Ambion). Wild type and mutant inserts were confirmed by sequencing and are listed. 293 IL-I RITLR4/MD2 cells were transfected with 10 ng of each firefly luciferase reporter, 10 ng of pCSK-lacZ vector and 300 ng of cmv-146A or cmv-146B. To construct cmv-146A or cmv-146B vectors -300 bp fragments containing pre-mir-146a or pre-miR-146b, respectively, were amplified from human genomic DNA and cloned into cDNA3 vector. When transfected into 293 IL-1 R/TLR4/MD2 cells, these constructs produce mature miRNA, as assessed by Northern blot and qPCR.

EXAMPLE 4

MiR-146a/b Downregulate Protein Expression Levels of

IRAK1 and TRAF6 mRNA

This example illustrates downregulation of protein expression levels of IRAK1 and TRAF6 in target cells by miR-146.

Stable, puromycin-resistant clones were generated that overexpress either mir-146a or a control microRNA encoding a "scrambled" mir-146a sequence (SEQ ID NO: 15). To generate the clones, THP-1 cells were infected with lentiviruses having the maps depicted in FIG. 4a. Northern blot analysis (FIG. 4b) revealed a strong upregulation of endogenous mir-146a in scramble control cells upon treatment with LPS, in contrast mir-146 overexpressing cells showed high level of exogenous mir-146 expression already without any treatment.

Figure 4:
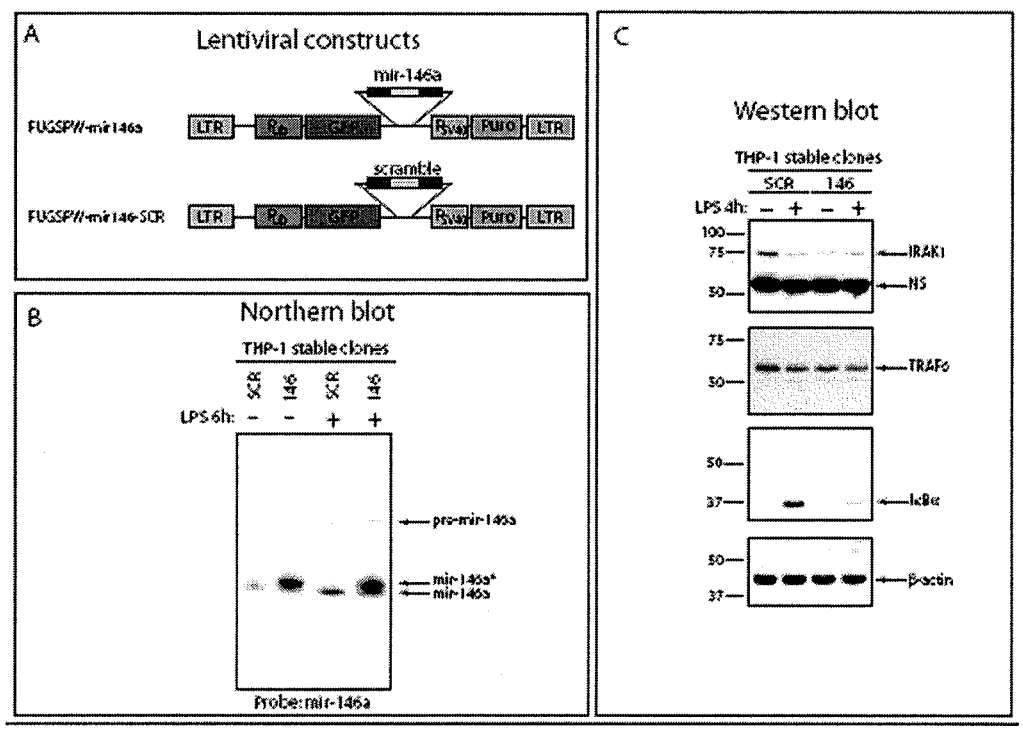
FIG. 4 shows downregulation of IRAK1 and TRAF6 protein levels by miR-146a. (*a*) Map of the lentiviral constructs used to create stable THP-1 clones overexpressing either miR-146a (top) or the control miR-146a "scrambled" (SCR) sequence (bottom). (*b*) Northern blot performed on the above mentioned stable THP-1 clones, showing levels of endogenous (mir-146a) and exogenous (mir-146a*) mir-146. SCR stands for Scramble; 146 for miR-146a. Cells were left untreated or treated with LPS 10 µg for 6 hours. (*c*) Western blot showing IRAK1 (first panel from the top) and TRAF6 (second panel from the top) protein levels are downregulated by overexpression of miR-146a in THP-1 cells. 50 micrograms of total protein was resolved on SDS-PAGE gel and transferred to nitrocellulose membrane. The membrane was probed sequentially with anti-IRAK1 antibodies (Santa Cruz), anti-TRAF6 antibodies (Santa Cruz) and anti-beta-actin antibodies (Santa Cruz) as loading control.

Expression of IRAK1 protein was significantly reduced in cells overexpressing mir-146a, compared to "scrambled" control cells (FIG. 4c). LPS treatment of the control cells resulted in downregulation of IRAK1 protein levels. Cells ectopically expressing mir-146a showed no further decrease in IRAK1 protein levels upon LPS treatment. TRAF6 protein levels were also decreased in cells expressing mir-146a, although the level of downregulation was less pronounced. Thus, an increase in mir-146 expression levels in the cells clearly downregulates protein levels of its target genes such as, for example, IRAK1 and TRAF6.

EXAMPLE 5

Treatment of Sepsis

This example illustrates the treatment of a patient suffering from sepsis.

A patient suffering from or at risk of developing sepsis is identified and administered an effective amount of a composition comprising a miR-146. A typical daily dose for a miR-146 of the present invention might range from about 0.01 µg/kg to about 1 mg/kg of patient body weight or more per day, depending on the factors mentioned above, preferably about 10 µg/kg/day to 100 10 µg/kg/day. The appropriate dosage and treatment regimen can be readily determined by the skilled artisan based on a number of factors including the nature of the miR-146, the route of administration and the patient's disease state. Sepsis treatment efficacy is evaluated by observing delay or slowing of disease progression, amelioration or palliation of the disease state, and/or remission.

All patents and publications are herein incorporated by reference in their entireties to the same extent as if each individual publication was specifically and individually indicated to be incorporated by reference.

The invention illustratively described herein suitably can be practiced in the absence of any element or elements, limitation or limitations that is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

What is claimed is:

1. A method for inhibiting signal transduction from an IL-1 receptor/Toll-like receptor, comprising:
   identifying an immune target cell in which NF-kB is activated; and
   administering a microRNA-146 (miR-146) oligonucleotide to the immune target cell, thereby inhibiting signal transduction from said IL-1/Toll-like receptor.

2. The method of claim 1, wherein the IL-1 receptor/toll-like receptor is selected from the group consisting of IL-1 receptor, Toll-like receptor 4 (TLR4), Toll-like receptor 2 (TLR2), and Toll-like receptor 5 (TLR5).

3. The method of claim 1, wherein the oligonucleotide comprises a sequence encoding a miR-146 selected from mature miR-146a (SEQ ID NO: 1) and mature miR-146b (SEQ ID NO: 3).

4. The method of claim 1, wherein the immune target cell is selected from the group consisting of a dendritic cell a macrophage, a helper T cell ($T_{h1}$ and $T_{h2}$) and a regulator T cell ($T_{reg}$).

5. The method of claim 1, wherein the production of at least one pro-inflammatory cytokine is dampened.

6. The method according to claim 5, wherein the cytokine is at least one cytokine selected from the group consisting of TNF and IL-1.

7. The method of claim 1, wherein the immune target cell is a cell involved in innate immunity.

8. The method of claim 1, wherein the miR-146 oligonucleotide comprises a modification selected from LNA, 2'-O-methyl, 2-O-methoxyethyl, and 2'-fluoro.

9. The method of claim 1, wherein the miR-146 oligonucleotide comprises a phosphorothioate modification.

10. The method of claim 1, wherein the miR-146 oligonucleotide is modified with cholesterol.

11. The method of claim 10, wherein the cholesterol is linked through a hydroxyprolinol linkage on the 3' end of the miR-146 oligonucleotide.

* * * * *